United States Patent
Jarvik

Patent Number: 5,738,626
Date of Patent: Apr. 14, 1998

[54] TWO-STEP CARDIOMYOPLASTY WITH VENTRICULAR REDUCTION

[76] Inventor: Robert Jarvik, 124 W. 60th. St., New York, N.Y. 10023

[21] Appl. No.: 661,342

[22] Filed: Jun. 14, 1996

[51] Int. Cl.$^6$ ................................................. A61N 1/362
[52] U.S. Cl. ........................... 600/16; 128/898; 600/37; 607/119; 623/3; 601/153
[58] Field of Search ........................ 600/16, 37; 607/119, 607/23; 128/897–899; 601/153; 623/3

[56] References Cited

U.S. PATENT DOCUMENTS

| | | | |
|---|---|---|---|
| 4,092,742 | 6/1978 | Kantrowitz et al. | 3/128 |
| 5,106,386 | 4/1992 | Isner et al. | 606/15 |
| 5,195,518 | 3/1993 | Mannion et al. | 600/16 |
| 5,205,810 | 4/1993 | Guiraudon et al. | 600/16 |
| 5,603,337 | 2/1997 | Jarvik | 600/16 |

*Primary Examiner*—Jennifer Bahr
*Assistant Examiner*—Rosiland Kearney

[57] ABSTRACT

Cardiomyoplasty is a high mortality procedure (fifty percent two year mortality) with limited hemodynamic benefit. Excision of left ventricular myocardium in dilated congestive heart failure is also a high mortality procedure (forty percent one year mortality), but is one which may produce significant hemodynamic improvement in some patients although it can produce fatal hemodynamic deterioration in other patients. Use of cardiomyoplasty following the resection of ventricular myocardial tissue to reduce the diameter of the ventricular chamber provides replacement muscle mass and permits the cardiomyoplasty to function more effectively. The invention provides a new operation to achieve low mortality, which combines the previous two procedures described above in such a way that the strengths of each procedure overcomes the weaknesses of the other. The new operation is performed by surgically reducing the size of the dilated left ventricle via excision of myocardial tissue and then in the second step by placing a cardiomyoplasty muscle wrap. In one embodiment of the invention, left ventricular assist device support is temporarily utilized during the of period of myoplasty muscle conditioning.

3 Claims, 3 Drawing Sheets

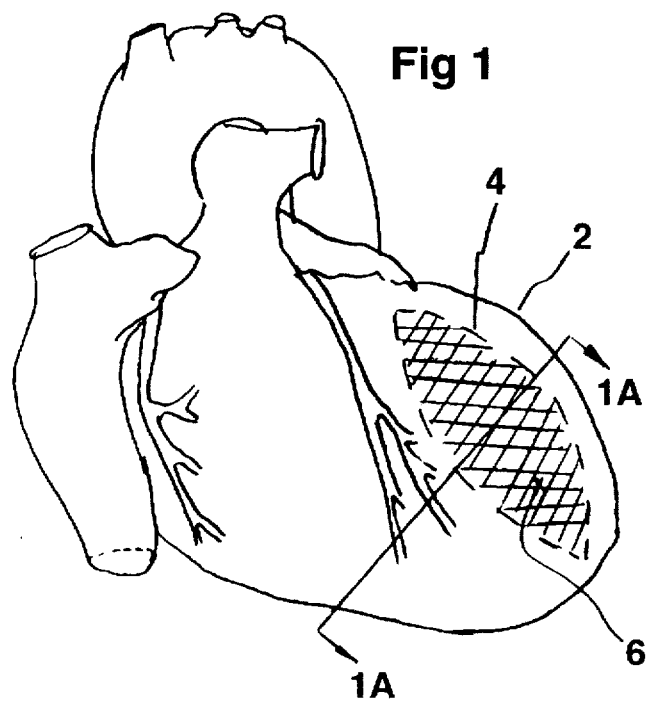
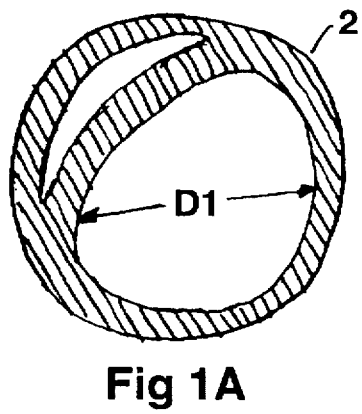
Fig 1
Fig 1A
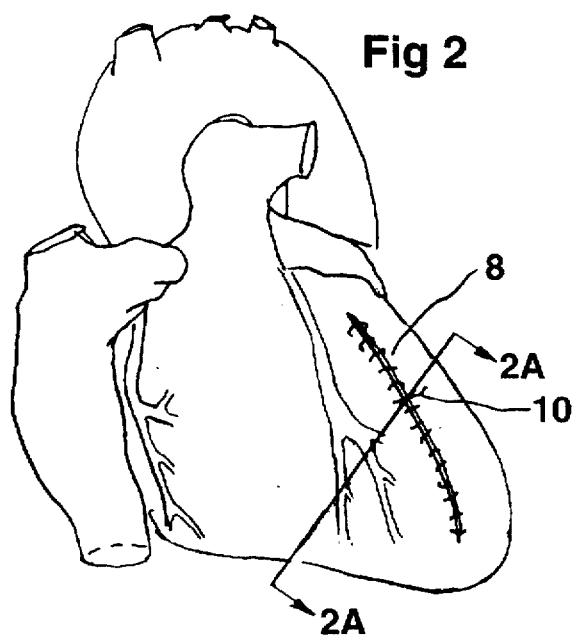
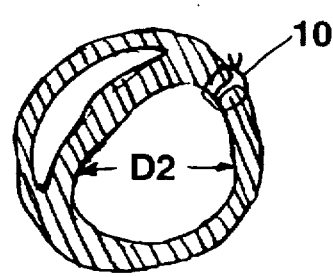
Fig 2
Fig 2A

TWO-STEP CARDIOMYOPLASTY WITH VENTRICULAR REDUCTION

BACKGROUND OF THE INVENTION

Congestive heart failure is a major cause of death and disability with limited treatment options. Presently, more than two million Americans suffer from various stages of congestive heart failure which has a very high mortality once deterioration to NYHA class IV occurs. Medical and pharmacological management of the disease has improved patient's prognosis, however congestive heart failure remains an extremely expensive disease and one in which hundreds of thousands die a death of prolonged suffering. Heart transplant is an extremely effective treatment for end-stage congestive heart failure, however this option is limited by the small number of donor hearts.

Over the past decade, cardiomyoplasty has been developed in which a skeletal muscle of the patient, such as the Latissimus Dorsi muscle is relocated form its natural site in the body, wrapped around the failing heart and stimulated electrically to produce the heart beat. The benefits of cardiomyoplasty are limited and the procedure carries nearly a fifty percent two year mortality. In my patent application Ser. No. #08/350-272, I disclosed a method of cardiomyoplasty in which the enlarged heart is first reduced in size through the effects of a left ventricular assist device and, thereafter the cardiomyoplasty muscle wrap procedure is performed. The major advantage of this procedure is that the natural heart functions much more efficiently at its normal size than it does when it is significantly enlarged. The amount of oxygen consumption by the myocardial muscle is related to the wall tension developed during ventricular contraction. The wall tension, in turn, is proportional to the fourth power of the diameter of the ventricular cavity and therefore at a smaller diameter less muscle work is used to pump a given volume of blood against a given blood pressure. Reducing the size of the ventricle prior to placing the muscle wrap reduces the wall tension and therefore helps the natural heart muscle to function. When the cardiomyoplasty is performed on an enlarged heart, if the heart improves, it will tend to become smaller. However, the muscle wrap itself does not become smaller and it will become loose and function poorly if the natural heart returns to its normal size. Therefore cardiomyoplasty performed on an enlarged heart is a self-limited procedure. In fact, many researchers in the field of cardiomyopathy have reported that the principle benefit of the procedure may be prevention of further dilatation of the natural ventricle because the myoplasty wrap acts as a "girdle."

For the cardiomyoplasty to work optimally the natural heart should be close to its normal size at the time the muscle wrap is performed. Thus, both the natural myocardial tissue and the muscle wrap tissue can contract at an efficient size. The natural myocardial tissue will be prevented from significant dilatation by the "girdle" effect of the muscle wrap tissue and the muscle wrap tissue can be placed at an appropriate wrap tightness to be both efficiently prestretched at end diastole for good muscle function and not be subject to loosening due to the natural heart shrinking within the muscle wrap.

Recently, a new operation introduced by Dr. Randas Batista has attempted to treat congestive heart failure by resecting a large portion of the left ventricular wall. In a group of about three hundred patients two-year mortality is reported to be about forty percent, although patient selection criteria, documentation of the stage of the patient's disease, and follow-up reporting are considered to be inadequate for a reasonable scientific conclusion of the efficacy of the procedure. However, some patients have survived between six months and two years following the procedure in reportedly improved condition.

Resection of large portions of the left ventricle has been common in cases of left ventricular aneurism. Some prior art efforts such as disclosed in U.S. Pat. No. 4,092,742, by Kantrowitz et al., have attempted to replace the function of excised myocardial tissue with mechanical replacements. However, Kantrowitz did not recognize the potential benefit of ventricular size reduction, and states "In patients with large infarctions or aneurysms, resection of the left ventricular myocardium impairs the contractility of the remaining muscle and diminishes its ability to eject an adequate blood supply into the systemic and coronary circulation. This latter condition may lead to failure when the heart is resuscitated." In the case of ventricular aneurism the tissue that is excised is either necrotic myocardial tissue or fibrotic scar tissue at the site of an old myocardial infarction. The objective of resection has been to avoid paradoxical motion of the left ventricular wall or to reduce the risk of ventricular rupture. Excising living myocardial tissue has been deliberately avoided. But in the case of resection of a large mass of living ventricular muscle, such as done by Batista, although the patient may benefit from decreased wall tension, the remaining muscle mass may be insufficient to sustain the life of the patient, and failure such as noted by Kantrowitz may occur. This is a likely cause of death in many of the patients undergoing Dr. Batista's procedure. Cardiomyoplasty is a high mortality procedure (fifty percent two year mortality) with limited hemodynamic benefit. Excision of left ventricular myocardium in dilated congestive heart failure is also a high mortality procedure, but is one which may produce significant hemodynamic benefits in some patients although it may produce fatal hemodynamic functional inadequacy in other patients. Use of cardiomyoplasty following the resection of ventricular muscle provides replacement muscle mass and permits the cardiomyoplasty to function effectively on a heart of near normal size which will not shrink further.

The new operation, which is the subject of this invention combines the previous two procedures in such a way that the strengths of each procedure overcomes the weaknesses of the other procedure. The new operation is performed by surgically reducing the size of the dilated left ventricle via excision of myocardial tissue and then in the second step by placing the cardiomyoplasty muscle wrap.

OBJECTS OF THE INVENTION

It is an object of the present invention to provide an effective new surgical treatment of congestive heart failure.

An additional object of the invention is to improve the hemodynamic effectiveness of cardiomyoplasty muscle tissue by optimizing the size of the muscle wrap.

Another object of the invention is to improve the hemodynamic function of the patient by reducing the diameter of the left ventricle by excising left ventricular myocardium and then replacing muscle mass thus lost with living contracting skeletal muscle tissue via the cardiomyoplasty.

Another object of the invention is to provide a method of left ventricular apical cannulation for the use of a temporary left ventricular assist device in the period following the two-step cardiomyoplsty procedure while the skeletal muscle is electrically stimulated and conditioned to be able to sustain repetitive contraction at a normal heart rate.

THE DRAWINGS

FIG. 1 is a line drawing of a dilated heart such as is typical with congestive heart failure.

FIG. 1A is a sectional view of the heart taken along plane 1A—1A of FIG. 1.

FIG. 2 is an illustration of the reduction in size of the heart after a portion of the left ventricular myocardium is excised.

FIG. 2A is a sectional view of the heart taken along plane 2A—2A of FIG. 2.

Figure 6:
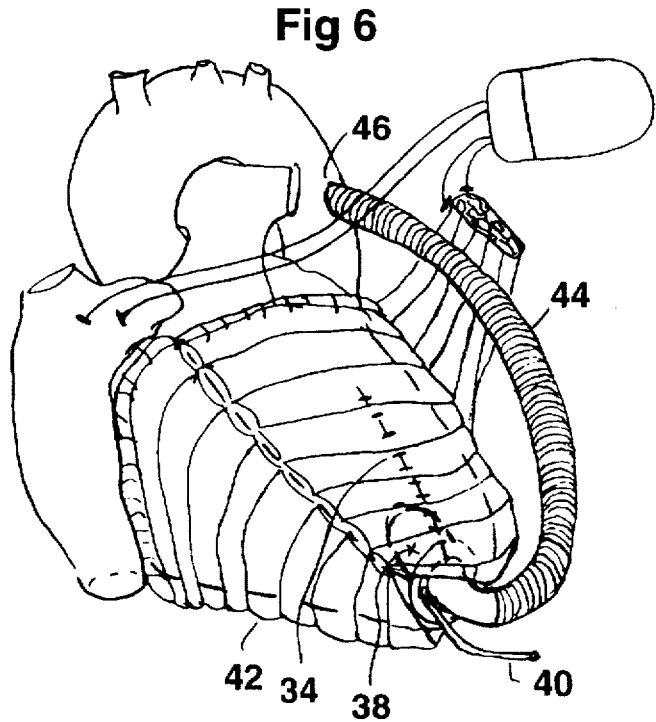
FIG. 6 illustrates a completed combined procedure in which a two-step cardiomyoplasty with ventricular reduction and placement of a left ventricular assist device is performed.
Figure 6A:
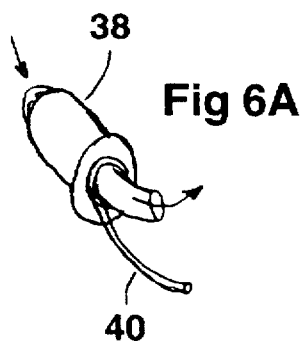

FIG. 6A as a drawing of an intraventricular left heart assist device as illustrated in dotted lines in FIG. 6.

DESCRIPTION OF THE INVENTION

The invention utilized a new surgical procedure which the dilated left ventricle is first reduced in size via myocardial resection and then is supported by a placement of cardiomyoplasty muscle wrap. In a further embodiment of the invention the surgical technique is modified to permit temporary implantation of a left ventricular assist device at the time the two-step procedure is performed.

Referring to FIG. 1 and FIG. 2, it is seen that the resection of myocardial tissue utilized a generally elliptical incision on the anterior wall of the left ventricle placed so as to avoid damage to the mitral valve, papillary muscles, or major coronary arteries. Closure of the ventricle after this incision is made and the myocardial tissue is removed results in a significant reduction of the diameter of the ventricle as reported by Dr. Batista and others.

Specifically referring to FIG. 1 the large left ventricle 2 has the characteristic shape of the heart in failure with cardiomegaly. A sectional view of the left ventricle and part of the right ventricle along plane 1A is shown in FIG. 1A. The diameter of the left ventricular cavity labelled D1 in FIG. 1A is markedly enlarged. The general position of an elliptical incision 4 in the left ventricular wall is illustrated by dotted lines. The incision is similar to the incision used for the past several decades in ventricular aneurysmectomy. An example of the incision from the early literature is seen in illustrations on page 238 of the Ciba Collection of Medical Illustrations, Volume 5, by Frank Netter, M.D., published in 1969. By utilizing this incision a generally elliptical portion of myocardium 6, illustrated by the cross-hatched lines in FIG. 1, is removed from the left ventricular wall. The only essential difference between this and the long practiced procedure of ventricular aneursmectomy is the fact that with the new procedure viable myocardial tissue is deliberately resected whereas with standard aneurism resections the intention is to primarily remove scar tissue or necrotic myocardial tissue while avoiding removal of viable myocardial muscle.

FIG. 2 illustrates the reduction in size of the left ventricle after removal of the segment of muscle 6. The closed incision 8 is held together by sutures, one of which is shown at 10. This reduces the size of the left ventricular cavity to a diameter D2 illustrated in FIG. 2A. Note that diameter D2 is significantly smaller than diameter D1, which results in the decreased wall tension and decreased myocardial oxygen consumption. Most likely this is an important reason for benefit obtained from the procedure. Its relative reduction in diameter is illustrated in an article appearing on page A16 of the Jun. 14th 1996 New York Times. A typical reduction is from a diameter of approximately 3.3" before the myocardial resection to a diameter of approximately 2.4" after the resection.

Figure 3:
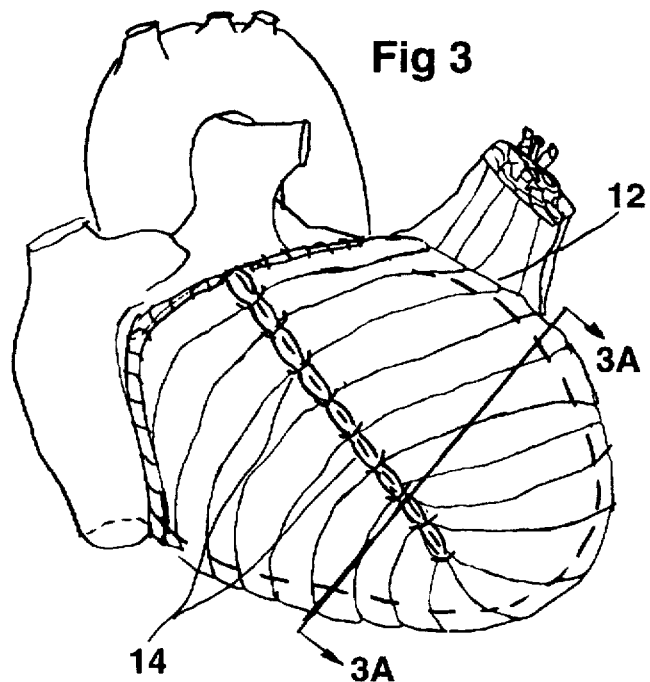
FIG. 3 is an illustration of a cardiomyoplasty performed on a dilated heart.
Figure 3A:
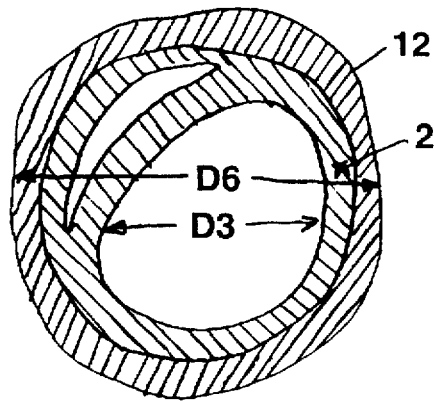
FIG. 3A is a sectional view of the heart taken along plane 3A—3A of FIG. 3.
Figure 4:
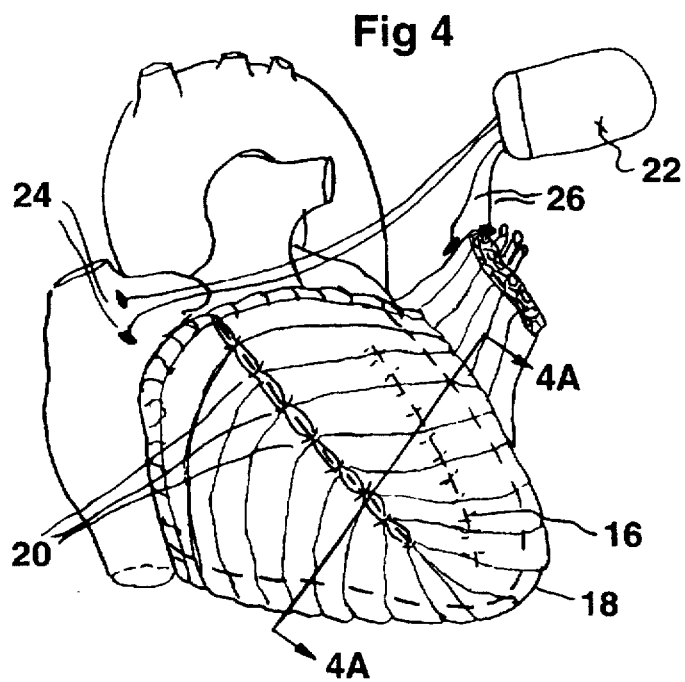
FIG. 4 is an illustration of the heart following the two-step cardiomyoplasty with ventricular reduction procedure.
Figure 4A:
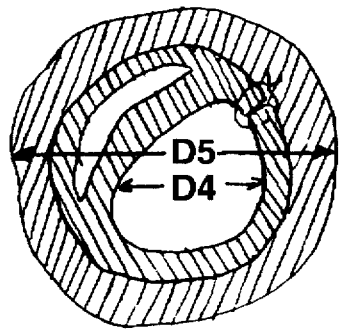
FIG. 4A is a sectional view of the heart taken along plane 4A—4A of FIG. 4.

FIG. 3 is an illustration showing a myoplasty muscle wrap comprised of Latissimus Dorsi muscle 12 wrapped around the heart and held in the wrapped position by a suture line 14. FIG. 3A shows the natural ventricular tissue within the muscle wrap tissue 12. The myoplasty procedure does not decrease the diameter of the left ventricle D3, and therefore in itself does not provide benefits related to reduction of this diameter and reduction of wall tension. FIG. 4 illustrates the heart at the completion of the procedure according to the present invention. In this procedure, a section of viable myocardial tissue is removed from the left ventricular wall in a similar fashion to that illustrated in FIGS. 1 and 2. The result is a heart with the left ventricle reduced in size, having a diameter (D4 FIG. 4A) close to the diameter of a normal left ventricle. The suture line closing the incision in the left ventricle 16 is then covered with the muscle wrap tissue 18. The muscle wrap is held in place around the heart by suture line 20. The myoplasty procedure requires a myostimulator 22 with appropriate sensing electrodes 24 and stimulating electrodes 26. As a result of this combined procedure, not only is the diameter of the left ventricle D4 reduced, but the diameter of the muscle wrap D5 is also significantly smaller than that which would have been necessary if the myoplasty procedure were performed on a dilated ventricle (as illustrated by diameter D6 in FIG. 3A). An additional advantage of this procedure is that it permits complete wrapping of the ventricle with a smaller length of Latissimus Dorsi muscle. This is especially important when the length of muscle available in the patient is relatively short.

The new two-step cardiomyoplasty operation with ventricular myocardial resection combines two high mortality operations in an inventive way where the weaknesses and failings of each operation are supported by the strengths and benefits of the other operation. Thus, while neither of the previous operations alone accomplishes both ventricular size reduction and augmentation of muscle mass the operation of the new invention does. This is the same objective as was previously disclosed in my application entitled "Two-Stage Cardiomyoplasty." The method of the present invention has the advantage that it can be performed at one time.

Figure 5:
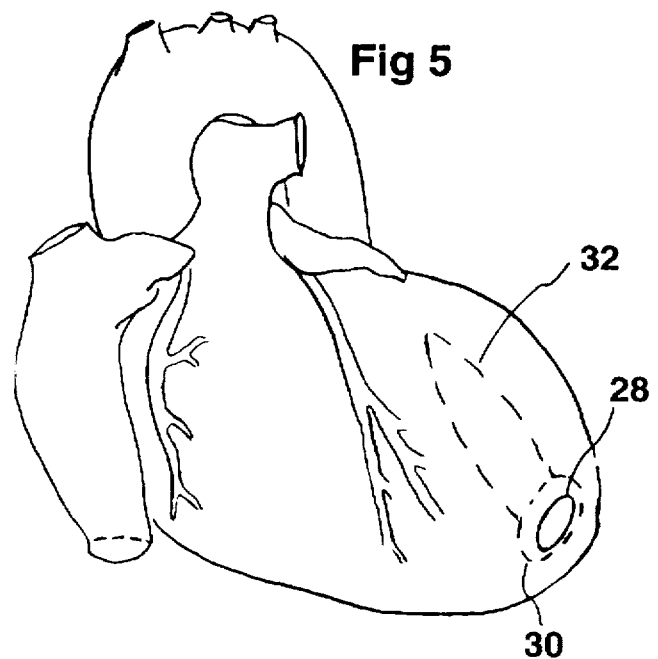
FIG. 5 is an illustration of the size and position of the left ventricular apical core utilized with implantation with left ventricular assist devices and showing the new method of combined coring and ventricular myocardial wall excision of the present invention.
Figure 5A:
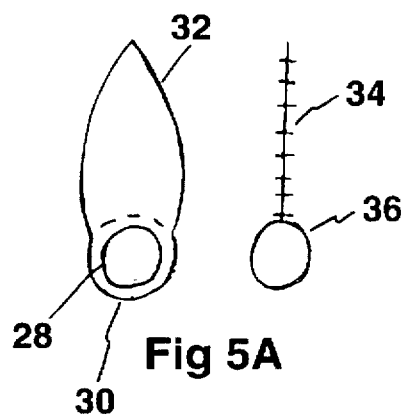
FIG. 5A is an illustration of the incisions shown in FIG. 5 before and after suturing.

One disadvantage of any cardiomyoplasty procedure is that the tissue used is skeletal muscle, which fatigues on repeated stimulation at normal heart rates. A period of time of exceeding several weeks is required to condition the skeletal muscle and transform the muscle to a different tissue rich in mitochondria and adapted to withstand repeated stimulation with much less fatigue. An additional embodiment of the present invention provides a temporary left heart assist device that can support both the remaining left ventricular myocardial tissue and the myoplasty tissue by reducing the necessary work-load of both while the patient recovers and the myoplasty muscle is conditioned. FIG. 5 illustrates a new surgical method to accomplishing this. Implantation of a left ventricular assist device using apical cannulation presently relies on use of a round coring knife to remove a small plug of tissue out of the ventricular apex. Either the cannula for the inflow of a ventricular assist pump or the pump itself in the case of a miniaturized axial flow pump is then implanted within the hole cut with the coring knife. The size of this hole is illustrated relative to the size of the left ventricle in FIG. 5 and FIG. 5A, shown by the circle 28. The necessary size of the core of muscle tissue removed is generally approximately two centimeters in diameter. If a temporary ventricular assist device is to be implanted in conjunction with the new two-step cardiomyoplasty procedure a larger coring knife having a dimension of approximately 3 to 4 centimeters diameter is used to make a hole of the relative size indicted at 30 in FIG. 5 and FIG. 5A. The generally elliptical incision which is an extension of the cored hole made in the left ventricular is illustrated at 32. This is then closed by suture line 34, leaving the proper diameter hole 36 for insertion of the assist device or inflow cannula. FIG. 6 illustrates the heart after the procedure is completed. In this illustration an intraventricular axial flow pump left heart assist device 38 is positioned in the apex of the left ventricle and is powered by power cable 40, which provides electricity from a remote source. The muscle wrap 42 surrounds the natural ventricles and is parted at the apex where the outflow of the assist device exits the heart. Blood enters the assist device through an inlet opening within the left ventricle and is pumped via an outflow vascular graft 44 to the aorta at 46. Thus, this procedure provides the ability to combine resection of a portion of the left ventricle with both the proper geometry for insertion of the heart assist device and the ability to perform the muscle wrap so as to permit later removal of the assist device.

The information disclosed in the description of the present invention is intended to representative of the principles that I have described. It will thus be seen that the objects of the invention set forth above and those made apparent from the preceding description are efficiently obtained and that certain changes may be made in the above articles and constructions without departing from the scope of the invention. It is intended that all matter contained in the above description or shown in the accompanying drawings shall be interpreted as illustrative but not in a limiting sense. It is also understood that the following claims are intended to cover all of the generic and specific features of the invention herein described and all statements of the scope of the invention, which is a matter of language, might be said to fall there between.

Thus having described my invention I claim:

1. The method of two-step surgical treatment of dilated congestive heart failure comprised of:
    a) excising left ventricular myocardial tissue utilizing one or more incisions
    b) suturing the remaining myocardial tissue so as to reduce the diameter of the left ventricular chamber, and,
    c) performing a cardiomyoplasty after completion of reduction of the diameter of the left ventricular chamber.

2. The method of two-step surgical treatment of dilated congestive heart failure comprised of:
    a) excising a portion of the dilated left ventricular myocardial tissue,
    b) partially suturing the myocardial tissue closed so as to significantly reduce the diameter of the left ventricular chamber while leaving an opening,
    c) implanting a mechanical left ventricular assist device including a tubular conduit, utilizing said opening as a route for said assist device to pump blood from the left ventricle through said conduit into the aorta,
    d) performing a cardiomyoplasty,
    e) running said left ventricular assist device during the period of cardiomyoplasty conditioning, and,
    f) re-operating and removing the left ventricle assist device after myoplasty conditioning.

3. The method of two-step surgical treatment of congestive heart failure of claim 2 in which a coring knife is used to make a hole in the myocardium and incisions communicating with are utilized to excise additional myocardial tissue.

* * * * *